United States Patent [19]
Taylor

[11] Patent Number: 5,389,514
[45] Date of Patent: Feb. 14, 1995

[54] METHOD FOR SPECIFICALLY ALTERING THE NUCLEOTIDE SEQUENCE OF RNA

[75] Inventor: John Taylor, Cheltenham, Pa.

[73] Assignee: Fox Chase Cancer Center, Philadelphia, Pa.

[21] Appl. No.: 937,490

[22] Filed: Aug. 28, 1992

[51] Int. Cl.$^6$ .......................... C12Q 1/69; C12Q 1/02; C12P 19/34

[52] U.S. Cl. ......................................... 435/6; 435/29; 435/91.1; 435/91.3; 435/91.32; 435/91.5; 435/91.51

[58] Field of Search ............................. 435/6, 91, 29; 536/24.5; 935/77, 78

[56] References Cited

PUBLICATIONS

Casey et al. P.N.A.S. 89: 7149–7153, 1992.
Araya et al. P.N.A.S. 89: 1040–1044, 1992.
H. Zheng et al., Journal of Virology, 66: 4693–4697 (1992),
R. Heiermann et al., Nucleic Acids Research, 13: 2709–2730 (1985).
J. Manley, Proc. Natl. Acad. Sci. USA, 77: 3855–3859 (1980),
J. Glenn et al., Journal of Virology, 64: 3104–3107 (1900).
J. Haseloff et al., Nature, 334: 585–591 (1988).
F. Cameron et al., Proc. Natl. Acad.Sci, USA, 86: 9139–9143 (1989).
R. Wagner et al., Proc. Natl. Acad. Sci., USA, 86: 2647–2651 (1989).
C. Sureau et al., Journal of Virology, 63: 4292–4297 (1989).
G. Luo et al., Journal of Virology, 64: 1021–1027 (1990).
M. Chao et al., Journal of Virology, 64: 5066–5069 (1990).
M. Chao et al., The Hepatitis Delta Virus, Wiley–Liss, Inc., pp. 275–281 (1991).
J. Taylor et al., Journal of Hepatology, 13: S119–S120 (1991).
R. Cattaneo, Experientia, 46: 1142–1148 (1990).
V. Walbot, Trends in Genetics, 7 (1991).
P. Hodges et al., Trends in Biochemical Sciences, 17 (1992).
R. Hurlbert et al., the Journal of Biological Chemistry, 235: 443–449 (1960).
N. Salzman et al., Journal of Biological Chemistry, 230: 1001–1012 (1958).

Primary Examiner—Margaret Parr
Assistant Examiner—Kenneth R. Horlick
Attorney, Agent, or Firm—Dann, Dorfman, Herrell and Skillman

[57] ABSTRACT

A method is provided for specifically altering the nucleotide sequence of an RNA molecule. As performed in vitro the method comprises: (1) selecting a target sequence in an RNA molecule; (3) hybridizing the target sequence with a complementary nucleic acid, either DNA or RNA, thereby forming a double-stranded structure; (4) incubating the hybrid molecule with a cellular extract which contains components capable of specifically converting U to C in an RNA molecule, when the U is disposed within a double-stranded structure. Incubation of the hybrid molecule with cellular extracts comprising the RNA editing component results in a specific alteration of the nucleotide sequence of the RNA at the target sequence. The method of the invention may also be applied in vivo. Complementary nucleic acids are introduced into cells and hybridized to the target sequence to form a double-stranded structure. The RNA editing components already present in the cell may then specifically convert U to C in the target sequence resulting in an alteration in the target RNA molecule.

13 Claims, No Drawings

METHOD FOR SPECIFICALLY ALTERING THE NUCLEOTIDE SEQUENCE OF RNA

Pursuant to 35 U.S.C. §202(c), it is hereby acknowledged that the U.S. Government has certain rights in the invention described herein, which was made in part with funds from the National Institutes of Health.

FIELD OF THE INVENTION

This invention relates to the field of RNA therapy. In particular, a method is provided for editing an RNA molecule by selectively converting uridine to cytidine in a target RNA sequence disposed within the RNA molecule.

BACKGROUND OF THE INVENTION

Recent advances in recombinant DNA technology have brought the substantial promise of gene therapy nearer to realization. Techniques for specifically altering the nucleotide sequence of a DNA molecule have been a particularly valuable development. These techniques enable a DNA molecule to be tailored to provide a specific selected effect, when provided as gene therapy.

An alternative to gene therapy is to manipulate gene expression at the RNA level. Targeting RNA has several advantages not inherent in gene manipulation at the DNA level. For example, RNA therapy can be targeted to cells and tissues where gene expression is actually occurring, i.e., cells in which mRNA encoding a specific gene product is being actively transcribed and translated. Additionally, in certain situations, RNA is a good target for gene therapy because RNA is an intermediate in reverse transcription, whereby certain viral DNA genomes are produced.

Already, RNA-targeted gene therapy has been accomplished through the use of anti-sense RNA molecules (RNA or DNA) designed specifically to block the translation of a target RNA molecule into protein. Assuming knowledge of the nature of the target mRNA molecule, complementary oligonucleotides are created to bind specifically to regions of the RNA molecule critical for selected functions of the molecule, such as maintenance of secondary structure or translation, thereby disrupting expression of the gene product encoded by the RNA.

Another type of RNA-targeted gene therapy involves the use of sequence-specific endoribonucleases, known as ribozymes, to achieve cleavage and inactivation of gene transcripts in vivo. According to this strategy, assuming knowledge of the mRNA transcribed by the gene, ribozymes can be synthesized which hybridize specifically to a predetermined sequence and cleave the RNA molecule at a specified site in the target sequence, so as to inhibit production of the gene product by destroying its messenger.

Both ribozymes and anti-sense molecules are capable of disrupting gene expression at the RNA level, ribozymes by targeted destruction of the specific RNA, and anti-sense molecules by disrupting secondary structure or blocking translation.

Although inhibiting gene expression is certainly a valuable mode of RNA therapy, it would be even better to have RNA-targeted methods for enhancing gene expression (by increasing the stability or translation efficiency of an RNA molecule) or altering the subsequently produced gene product. Such methods are available for DNA-targeted gene therapy (e.g., in vitro mutagenesis), but not for RNA-targeted gene therapy. Clearly, a method for altering the nucleic acid sequence of an RNA molecule could provide many new therapeutic methods by combining the advantages inherent in specifically altering DNA with the advantages of targeting RNA.

SUMMARY OF THE INVENTION

In accordance with the present invention, a method is provided for specifically altering the nucleotide sequence of an existing RNA molecule. This alteration is sometimes referred to herein as "RNA editing," and is accomplished by converting uridine to cytosine in a single stranded target sequence disposed within the RNA molecule. The target sequence comprises an editable segment which has at least one uridine (the "target nucleotide") disposed therein, and flanking segments, several nucleotides in length, which abut the editable segment on either side of the editable segment.

According to one aspect of the invention, adapted for in vitro use, the method comprises providing a single stranded nucleic acid (DNA or RNA) which has a sequence complementary to the target sequence. The RNA editing function is provided by a nuclear extract or a whole cell extract having a significant amount of nuclear material. In accordance with the present invention, such extracts have been found to possess one or more RNA editing components capable of converting uridine to cytidine when the uridine is disposed within a double-stranded nucleic acid structure at a position several nucleotides inward from each terminus of the double-stranded structure.

According to the method, the RNA molecule is hybridized with the complementary nucleic acid, thereby forming a hybrid molecule having a double-stranded structure made up of the target sequence and the complementary nucleic acid. The hybrid molecule is then treated with the nuclear extract having the RNA editing component, under conditions which promote conversion of uridine to cytidine when the uridine is disposed within a double-stranded nucleic acid structure. The RNA editing component then exerts its activity, thereby converting the uridines disposed within the editable segment to cytidines. In this way, the RNA molecule is specifically edited by converting uridine to cytidines in the editable segment of the target sequence disposed within the RNA molecule.

With prior knowledge of the sequence of the selected RNA molecule, any target sequence within that molecule may be selected for editing.

Nuclear extracts having the RNA editing component may be obtained from a variety of sources. In a preferred embodiment, whole cell extracts of Drosophila embryos are utilized in the editing process.

At least one uridine is disposed within the editable segment. The editable segment may comprise additional uridines, as long as the flanking segments are several nucleotides in length.

According to another aspect of the present invention, the complementary single stranded nucleic acid, which may be composed either of DNA or RNA, may be utilized in vivo. Cultured cells may be transfected with complementary nucleic acids of the invention. For intact multicellular organisms (e.g., mammals), in vivo delivery of the complementary nucleic acids to cells and tissues may be accomplished by methods such as those used for delivery of anti-sense or ribozyme molecules. For example, oligonucleotides may be delivered by targeted liposomes. Alternatively, target cells may be transformed with DNA molecules that, upon DNA-directed RNA transcription, form the appropriate complementary RNA to hybridize in vivo with the target RNA sequence.

The RNA editing method of the invention provides notable advantages over RNA therapy methods currently available. Similar to anti-sense and ribozyme technologies, the method of the invention can be used to disrupt the functionality of an RNA molecule. But, whereas anti-sense and ribozymes are limited only to disruption, the method of the invention can also be used to re-direct RNA functionality, e.g., to enhance the efficiency of an RNA molecule or to alter the structure of the protein produced by an RNA.

DETAILED DESCRIPTION OF THE INVENTION

The following words and phrases are defined, for reference in describing the invention, as follows:

1. RNA editing: refers to a specific alteration of the nucleotide sequence of an RNA molecule. In practicing the present invention, the nucleic acid sequence of a pre-determined target sequence of a selected RNA molecule is altered. The alteration comprises converting U in the editable segment of the target sequence to C, as described more fully below. The uridines targeted for editing are sometimes referred to herein as "target nucleotides."

2. Nuclear extract: refers to an extract of soluble components of isolated nuclei, or an extract of soluble components of whole cells of a type comprising a high percentage of nuclear material, or an extract of soluble components of whole cells, wherein the extract is prepared so as to be enriched in components normally residing in the cell nucleus.

3. RNA editing component: refers to one or more components in a nuclear extract, as defined above, capable of converting uridine to cytidines when the uridine is disposed within a double-stranded nucleic acid structure at a position several nucleotides inward from each terminus of the double-stranded structure. The target uridine could be disposed as few as 2–4 nucleotides inward from the terminus of the double-stranded structure, or it may be embedded within hundreds of base pairs of double-stranded structures.

The RNA editing component may be comprised of one or more sub-components. Therefore, for purposes of the present invention, the term "RNA editing component" refers to either a singular component or a plurality of components.

4. Double-stranded structure: refers to a complementary-base-paired double-stranded nucleic acid. In practicing the present invention, the double-stranded nucleic acid may consist of an RNA-DNA hybrid or an RNA-RNA hybrid.

In accordance with the present invention, it has been discovered that nuclear extracts, or whole cell extracts of cells which contain a high percentage of nuclear material, contain a component which is capable of editing RNA. This editing function comprises converting uridine to cytidines under prescribed conditions, and was first discovered in the study of editing of the Hepatitis Delta Virus (HDV) RNA genome. Zheng et al., J. Virol., 66:4693–97 (August 1992). Examining the naturally-occurring phenomenon of a U to C conversion at position 1012 of the HDV genome during replication, it was discovered that the change from U to C at this position occurs independent of any viral gene products. In fact, it was found that extracts containing a high percentage of nuclear material were capable of editing the HDV genome at position 1012 in the same manner as observed in intact cells infected with HDV. Editing was observed with extracts of Drosophila embryos, HeLa cells or calf kidney cells. The modification of position 1012 was found to occur in the absence of RNA replication, and, therefore, was proven to be an editing reaction, rather than a misincorporation of C for U during RNA-directed RNA synthesis.

It was further discovered that the entire HDV genome was not necessary for the modification by nuclear extracts to occur. However, the double-stranded rod-like structure of the HDV genome was required at the site of conversion, indicating that a double-stranded structure is necessary for the RNA editing component of the nuclear extracts to function. It should be noted that the modified U of the HDV genome is embedded in 10 consecutive base pairs of double-stranded structure.

Following the aforementioned observations in connection with HDV, it has been further discovered in accordance with the present invention that even non-viral RNA may be specifically edited by nuclear or high-nucleus-containing cellular extracts. The editing is a direct conversion of U to C, which may be due to amination of uridine to cytidines. Even though any RNA sequence appears to be a potential target for the editing function, the target uridine must be embedded in double-stranded structure, such as the 10 paired bases of the HDV genome around position 1012, which can be achieved by hybridization with either DNA or RNA.

It is likely that more than one uridine may be edited by the RNA editing component of nuclear extracts. However, the editable uridines must be flanked on either side by double-stranded structure.

Although the agent responsible for the editing function of the aforementioned nuclear or cellular extracts has not been elucidated, it may prove to be attributable to the enzyme cytidines synthase, which converts UMP to CMP and UTP to CTP, both reactions being essential to all cells. It has been discovered that glutamine is the amino donor for both the cytidines synthase and the RNA editing function. Moreover, both reactions are inhibited by the glutamine donor inhibitor, deazo-oxo-norleucine. Furthermore, a line of cultured Chinese hamster lung cells, which lacks cytidines synthase, has also been found unable to edit RNA.

Regardless of the identity of the specific factor(s) responsible for the RNA editing function of nuclear extracts, it is clear that nuclear extracts, or whole cell extracts containing a large percentage of nuclear material, possess the RNA editing function in sufficient quantity to effectively edit target RNA sequences, as will be described in greater detail below.

Various embodiments of the RNA editing method of the invention are described below. Any molecular cloning or recombinant DNA techniques not specifically described are carried out by standard methods, as generally set forth, for example, in Sambrook et al., "DNA Cloning, a Laboratory Manual," Cold Spring Harbor Laboratory (1989).

RNA molecules having a selected target sequence may be isolated from any biological source, such as solid tissues, body fluids, such as blood, lymph, urine, and the like, cultured cells, or microorganisms. Total RNA is isolated and purified by procedures commonly known in the art. For example, total nucleic acids may be isolated from cells by the use of sodium dodecyl sulfate (SDS) and pronase, followed by a phenol extraction and two ether extractions. Nucleic acids are then collected by ethanol precipitation, digested with a DNase (e.g., RQ DNase I, Promega Biotech) then extracted once more and precipitated with high-salt ethanol. A variety of other RNA isolation methods will be apparent to one skilled in the art.

Specific RNA fractions may also be purified using known procedures. For example, poly(A)+ RNA may be recovered from total RNA by passage over a poly(U) or oligo(dT) column, using procedures supplied by manufacturers of such column materials (e.g., Pharmacia Chemicals, Inc., Piscataway, N.J.).

It should be apparent to those skilled in the art that the source of the RNA is selected on the basis of the RNA molecules targeted for editing. For example, if it is desired to modify the expression of mRNA encoding a liver-specific enzyme, liver tissue or cells should be selected for obtaining RNA.

After RNA has been isolated and purified, it may be stored for future use under ethanol at −20° C., for example. The RNA is then collected by centrifugation, dried and resuspended in a suitable biological buffer, such as TE buffer (10 mM Tris-HCl, 0.1 mM EDTA) just prior to use.

Assuming knowledge of at least portions of the RNA molecule desired to be modified, any target sequence may be selected for editing. For example, a portion of an mRNA which encodes a structural feature of the gene product may be targeted for modification, thereby to change, enhance or interfere with the formation of that gene product. Alternatively, a portion of an mRNA encoding a signal or transit peptide, required for transport across biological membranes, may be targeted for modification to improve or disrupt such transport. Similarly, the translation start site itself may be modified (e.g., AUG to ACG).

The criteria for selecting a suitable target sequence are: (1) that it comprises a "editable" segment having at least one uridine disposed therein; and (2) the editable segment is flanked on either side by flanking sequences several (at least 5, in a preferred embodiment) nucleotides in length. These criteria are important for the practice of the present invention, so that the target sequence may be hybridized to a complementary nucleotide sequence, thereby forming the requisite double-stranded structure necessary for activity of the RNA editing component of the nuclear extract. It should be appreciated that the flanking segments may comprise uridines; however, these uridines generally will not be edited by the RNA editing component of the nuclear extract.

The single-stranded complementary nucleic acid used to form the requisite double-stranded structure can be either DNA or RNA. It may be prepared by any of several common methods known in the art. For example, complementary oligonucleotides may be prepared by PCR amplification of existing sequences. Alternatively, they may be chemically synthesized (e.g., via phosphoramidite chemistry) using commercially available reagents and apparatus. Oligonuceotides may also be modified, e.g., such that they possess increased stability in a cellular environment (particularly important for RNA), or are targeted to a particular tissue, or are more efficiently transported across a cell membrane. Preferably, the synthetic oligonucleotides should be complementary to the entire target sequence, so that they are capable of forming the double-stranded structure necessary for activity of the RNA editing component of the nuclear extracts.

Single-stranded complementary nucleic acids may be stored lyophilized, or under ethanol, or dissolved in a suitable biological buffer, such as TE buffer.

Suitable nuclear or cellular extracts having the RNA editing component may be obtained from a variety of sources. In preferred embodiments, cell extracts designed for use in in vitro eucaryotic transcription are particularly convenient and useful for practicing the present invention. For example, extract of Drosophila embryos supplied in the in vitro eucaryotic transcription kit available from Stratagene (La Jolla, Calif.) contains the RNA editing component(s) capable of converting U to C, according to the present invention. Preparation of a Drosophila embryo extract was disclosed by Heierman et al., Nucl. Acids Res., 13:2709–30 (1985). Another suitable cell extract is a HeLa cell lysate, supplied with the eucaryotic transcription system sold by Bethesda Research Laboratories (Gaithersburg, Md.). Preparation of a HeLa cell lysate was disclosed by Manley et al., Proc. Natl. Acad. Sci. USA, 77:3855–59 (1980).

It should be apparent to those skilled in the art how to obtain suitable cell extracts from other cell types. Such methods are commonly known in the art and will be readily apparent to practitioners in the field. Moreover, many of these cell extracts are commercially available. Cell extracts from sources other than those mentioned above may be compared with extracts having known RNA editing function, to determine if they also contain effective amounts of the RNA editing component.

The method of the invention involves creating a double-stranded nucleic acid structure in the target sequence. To accomplish this, any preexisting secondary structure in the RNA molecule may need to be disrupted, thereby rendering the target sequences contained therein hybridizable. Many methods are available for denaturing double-stranded nucleic acid structures. For purposes of the present invention, it is preferable to denature the RNA by means which avoid chemical modification. For example, samples containing RNA may be heated to 65°–95° C. for 2–3 minutes, then quickly cooled by placing in an ice bath.

The denatured RNA molecule comprising the target sequence may be hybridized with the complementary nucleic acid according to standard methods. For example, RNA comprising the target sequence and the complementary nucleic acid may be combined in the presence of appropriate salts, heated to 65° C., then slowly cooled to room temperature, thereby effecting hybridization of the target sequence with the complementary nucleotide sequence.

The hybrid molecule is then treated with the nuclear extract by combining them in a suitable biological buffer, such as 50 mM Tris-HCl, pH 7.9, 6 mM $MgCl_2$, 40 mM $(NH_4)_2SO_4$, 0.2 mM EDTA, 1 mM dithiothreitol and 15% glycerol (see Manley et al., supra), or 10 mM Hepes-KOH, pH 8.0, 8.5 mM $MgCl_2$, 120 mM KCl 0.5 mM dithiothreitol and 20% glycerol (see Heiermann et al., supra). In a preferred embodiment, nuclear extracts are used at concentrations equivalent to those used for eucaryotic in vitro transcription, according to instructions provided by suppliers of such in vitro transcription kits, as described above. In a preferred embodiment, a 25 µl reaction mixture contains 100 ng of the hybrid molecule. The reaction mixture is incubated for up to 16 hours at 20°–37° C. In a preferred embodiment, the incubation is performed at 30° C. for 30 minutes. Reactions may be terminated by phenol/ether extraction of each sample, as described above, followed by precipitation of the RNA with ethanol.

Editing of the target RNA sequence can be verified by DNA sequence analysis of the target RNA sequence, after it has been reverse-transcribed and amplified by polymerase chain reaction (PCR). Suitable primers may be constructed for PCR, according to methods well known in the art. The nucleotide sequence of the amplified DNA product is determined according to well known methods.

In an alternative embodiment for verification of editing, if the editing results in the introduction or removal of a DNA restriction site, this may be utilized to verify the editing by a simple electrophoretic method, not involving DNA sequencing. In this embodiment, one of the PCR primers is end-labeled, thereby to form a detectable PCR product. The product is then digested with the appropriate restriction endonuclease, then separated by electrophoresis on an agarose gel. The relevant introduction or removal of the restriction site should readily be apparent, upon drying the gel and visualizing the change in mobility of the DNA segments by autoradiography.

Thus, target sequences of selected RNA molecules may be edited in vitro according to the methods set forth hereinabove. The method may be utilized to disrupt gene expression, enhance gene expression or modify the structure or function of a gene product.

The method of the invention may be modified for in vivo application, taking advantage of the observation, in accordance with the present invention, that intact cells can exert the RNA editing effect present in nuclear extracts, provided that the requisite double-stranded structure can be produced within those cells. For example, as disclosed by Zheng et al., J. Virol., 66: 4693–97 (August 1992), transfection of cultured cos 7 cells with HDV genome DNA or RNA resulted in editing of the RNA genome at position 1012, in the absence of any other viral functions. It should be noted in this connection that HDV genomes possess the requisite double-stranded structure at the editing position.

Hence, the method of the invention may be modified for in vivo application as follows. Complementary nucleic acid sequences, as described above, are synthesized and prepared for in vivo delivery, according to known methods. Such methods include, for example, virus mediated infection of target cells, or delivery by target-specific liposomes or targeted cellular carriers, such as erythrocyte ghosts. Methods for preparing tissue- or cell-specific liposomes or erythrocyte carriers are well known in the art, as are methods for encapsulating nucleic acids therein. See, e.g., Glenn et al., J. Virol., 64: 3104–07 (1990). Such methods are suitable for targeted in vivo delivery to cells or tissues of a variety of living, multicellular organisms, including mammals.

Alternatively, cultured cells may be transfected with the complementary nucleic acids, according to well known methods. See, e.g., Zheng et al., supra. The method of the invention has been performed in several cultured cell lines, including cos 7 monkey kidney cells, human liver cell lines HuH7 and HepG2, and the mouse fibroblast cell line 3T3, which are all widely available.

Once the complementary nucleic acids are present in the target cells, they can hybridize with the selected target RNA sequence, in the same way as ribozymes or anti-sense RNA molecules have been shown to do in vivo. See, e.g., Haseloff et al., Nature, 334:585–91 (1988) and Cameron et al., Proc. Natl. Acad. Sci. USA, 86: 9139–43 (1989). Once hybridized, the required double-stranded structure in the region targeted for editing is formed, thereby enabling the editing component present within the cell to exert its effect. Thus, in a manner similar to the mode of operation of anti-sense RNA and ribozymes, "editing" oligonucleotides may be introduced into target cells to provide RNA-targeted therapy in vivo. It should be appreciated by those skilled in the art that the choices of target sequences in vivo may be somewhat more limited than for in vitro applications. This is because the target RNA sequence preferably should not be part of any inherent higher order structure, such as base-pairing or association with a cellular protein.

The RNA editing methods and strategy of the present invention constitute an advantageous alternative to methods currently available for providing RNA therapy. Like existing methods (e.g., ribozymes and anti-sense molecules), RNA therapy may be directed to cells and tissues wherein gene expression is actually occurring. However, whereas current RNA therapy methods can only accomplish disruption of gene expression, the methods of the present invention provide a way to redirect gene expression. For example, an RNA molecule can be edited to enhance its stability or efficiency of translation, or to actually alter the structure or function of a gene product. These advantages should lead to significant advances in the field of gene therapy.

The following examples are provided to describe the invention in further detail. These examples are intended merely to illustrate and not to limit the invention.

EXAMPLE 1

In Vitro Editing of Target RNA Sequences

The following are examples of substrates that have been tested for in vitro RNA editing according to the present invention. In each example, the target nucleotide is in bold type and underlined.

1. Natural HDV substrate, Sequence I.D. Nos. 1 (Top); 2 (Bottom)
   5'- . . . AGAGUAUAUCCUAUGGAAAUCC . . . -3'   Genomic HDV RNA
   3'- . . . CUUCCCGUAGGGUACCGAGGUG . . . -5'   Genomic HDV RNA
2. Modified HDV substrate, Sequence I.D. Nos. 1 (Top); 3 (Bottom)
   5'- . . . AGAGUAUAUCCUAUGGAAAUCC . . . -3'   Genomic HDV RNA
   3'- . . . UCUCAUAUAGGGUACCUUUAGG . . . -5'   Antigenomic HDV RNA
3. Modified HDV substrate, Sequence I.D. Nos. 1 (Top); 4 (Bottom)
   5'- . . . AGAGUAUAUCCUAUGGAAAUCC . . . -3'   Genomic HDV RNA
   3'-GTAGGGTACC-5'                                  Complementary RNA 10-mer
4. Non-HDV substrate, Sequence I.D. Nos. 1 (Top); 5 (Bottom)
   5'- . . . AGAGUAUAUCCUAUGGAAAUCC . . . -3'   Genomic HDV RNA
   3'-GTAGGATACC-5'                                  Complementary DNA 10-mer

| | | |
|---|---|---|
| 5. | Non-HDV substrate, Sequence I.D. No. Nos. 6 (Top); 7 (Bottom) | |
| | 5'-GGGAAGAGUAUAUCUCUAUGGAAAUCCCU-3' | 29-mer variation of HDV RNA |
| | 3'-CCCTTCTCATATAGTGATACCTTTAGGGA-5' | Complementary 29-mer DNA |

In vitro editing of the above-listed RNA target sequences was accomplished as follows. Single-stranded target RNA sequences were hybridized with complementary nucleic acids according to standard methods. Extracts from Drosophila embryos were purchased from Stratagene. Nuclear extracts of HeLa cells are commercially available from Promega Biotech, Madison, Wisconsin. In vitro editing reactions were performed by placing, e.g., 100 ng of the hybrid nucleic acid in, e.g., 25 μl nuclear extract, and incubated for 30 minutes at 30° C. Nucleic acids were then recovered by phenol extraction followed by 2 ether extractions, ethanol precipitation, digestion with RQ DNase I (Promega Biotech) and an additional extraction and ethanol procipitation.

To verify the editing of the target nucleotide in substrates 1-4 above, the target sequences were reverse-transcribed to form cDNA, then amplified by PCR. The PCR product of Sequence I.D. No. 1 of substrate 1 was sequenced by a dideoxy nucleotide sequencing procedure, using one of the PCR primers and a Sequenase kit (U.S. Biochemical) with the products resolved on a sequencing gel of 6% polyacrylamide. Additionally, substrates 1-4 were tested for cleavage by NcoI restriction endonuclease, since editing of the target nucleotide introduces an coNCOI restriction site in all four target sequences. See Zheng et al., supra.

Substrate 5, comprising target RNA Sequence I.D. Nos. 5 and 7 was too small for PCR amplification. Therefore, an alternative method for verifying RNA editing was employed. The RNA strand of Sequence I.D. No. 6 was labelled with [α-$^{32}$P]UTP, and the RNA editing reaction was carried out as described above. The RNA was then digested with nuclease P1 (Sigma) and subjected to thin-layer chromatography using Solvent 2 disclosed by Wagner et al., Proc. Natl. Sci. USA, 86: 2647-51 (1989) to measure the conversion of uridine to cytosine. Radioactivity was detected either by autoradiography or with a Radioanalytic Imaging System (AMBIS, San Diego, Calif.).

Sequence analysis of the PCR-amplified substrates 1-4 above revealed that the target uridine had been converted to cytidines in each target sequence. The efficiency of conversion ranged from 5-60%, depending on the target RNA sequence and the particular nuclear extract utilized. For example, substrates 1 exhibited a 60% conversion of U to C when incubated with the Drosophila extract. It is possible that longer incubation times would result in even greater percentage of conversion.

Although the thin-layer chromatography procedure does not yield information regarding specific editing, it revealed that the target RNA sequence of substrate 5 was edited by the nuclear extract in vitro, based on the appearance of radiolabelled cytidines during the incubation.

EXAMPLE 2

Editing of Target RNA Sequences in Cultured Cells

Substrate 1 from Example 1 above was tested for the ability to be edited in cultured cells, according to the present invention. Transfection was accomplished by means of a calcium phosphate procedure, according to standard methods. For RNA transfections, Lipofectin (BRL) was used. Cos 7 and related cell lines were used as host cells for the transfections.

Following transfection, cells were maintained 3-18 days according to standard methods, then total nucleic acids were isolated from the transfected cells. This was accomplished by use of sodium dodecylsulfate and pronase, followed by a phenol extraction and two ether extractions. Samples were collected by ethanol precipitation, digested with RQ DNase I (Promega Biotech), then extracted once more with phenol and ethanol precipitated. Editing of the target RNA sequence was verified by reverse transcription and PCR amplification, as described in Example 1 above. Editing of the target RNA sequence was observed as early as 3 days (the earliest time examined) and increased to 18 days after transfection. At 3 days after transfection, approximately 10-18% of the target RNA sequence was modified to comprise C instead of U. At 18 days after transfection, 21-33% of the target RNA sequences was edited.

The present invention is not limited to the embodiments specifically described and exemplified above, but is capable of variation and modification without departure from the scope of the appended claims.

What is claimed is:

1. A method for specifically editing an RNA molecule by converting uridine to cytidine in a target sequence disposed within said RNA molecule, said target sequence being at least 10 nucleotides in length and having a uridine disposed therein, at least two nucleotides inward from each terminus of said target sequence, said method comprising:
    a) providing a single stranded complementary nucleic acid having a sequence complementary to said target sequence;
    b) providing a nuclear extract having an RNA editing component which converts uridine to cytidine when said uridine is disposed within a double stranded nucleic acid structure of at least ten base pairs, at least two nucleotides inward from each terminus of said double stranded structure;
    c) hybridizing said RNA molecule with said complementary nucleic acid, thereby forming a hybrid molecule having a double stranded nucleic acid structure of at least ten base pairs, comprising said target sequence and said complementary nucleic acid; and
    d) treating said hybrid molecule with said nuclear extract having said RNA editing component, under conditions promoting conversion of uridine to cytidine when said uridine is disposed within a double stranded nucleic acid structure of at least ten base pairs, at least two nucleotides inward from each terminus of said double stranded structure, whereby said uridine disposed within said target sequence is converted to cytidine.

2. A method according to claim 1, wherein said uridine is disposed between 4 and 14 nucleotides inward from each terminus of said target sequence.

3. A method according to claim 1, wherein said complementary nucleic acid is provided in the form of DNA.

4. A method according to claim 1, wherein said complementary nucleic acid is provided in the form of RNA.

5. A method according to claim 4, wherein said nuclear extract is obtained from human HeLa cells.

6. A method according to claim 4, wherein said nuclear extract is obtained from Drosophila embryos.

7. A method according to claim 4, wherein said nuclear extract is obtained from calf kidney cells.

8. A method according to claim 1, wherein the step of treating said hybrid molecule with said nuclear extract is accomplished by:
    i) dissolving said hybrid molecule in said nuclear extract to form a solution; and
    ii) incubating said solution at a temperature of between about 20° C. and 37° C. for between about 15 minutes and 16 hours.

9. A method for specifically editing an RNA molecule in a cultured target cell by converting uridine to cytidine in a target sequence disposed within said RNA molecule, said target sequence being at least 10 nucleotides in length and having a uridine disposed therein, at least two nucleotides inward from each terminus of said target sequence, said method comprising:
   a) providing a single stranded complementary nucleic acid having a sequence complementary to said target sequence; and
   b) introducing said complementary nucleic acid into said cultured target cell under conditions promoting hybridization of said complementary nucleic acid to said target sequence, thereby forming a hybrid molecule having a double stranded nucleic acid structure of at least 10 base pairs, comprising said target sequence and said complementary nucleic acid, the formation of said hybrid molecule promoting conversion of uridine to cytidine when said uridine is disposed within said double stranded nucleic acid structure, at least two nucleotides inward from each terminus of said double stranded structure, whereby said uridine disposed within said target sequence is converted to cytidine.

10. A method according to claim 9, wherein said uridine is disposed between 4 and 14 nucleotides inward from each terminus of said target sequence.

11. A method according to claim 9, wherein said complementary nucleic acid is introduced into said cultured cell by transfection.

12. A method for specifically editing an RNA molecule by converting a target uridine disposed within said RNA molecule to cytidine, said method comprising:
   a) hybridizing said RNA molecule with a single stranded complementary nucleic acid at least 10 nucleotides in length, having a sequence complementary to a segment of said RNA molecule comprising said target uridine flanked on both sides by at least four nucleotides, thereby forming a hybrid molecule having a double stranded nucleic acid structure of at least ten base pairs, in which said target uridine is disposed at least four nucleotides inward from each terminus of said double stranded structure;
   b) providing a nuclear extract having an RNA editing component which converts uridine to cytidine when said uridine is disposed within a double stranded nucleic acid structure of at least ten base pairs, at least four nucleotides inward from each terminus of said double stranded structure;
   c) exposing said hybrid molecule to said nuclear extract to promote promoting conversion of said target uridine to cytidine, thereby specifically editing said RNA molecule.

13. A method for specifically editing an RNA molecule in a culture cell having an RNA editing component which converts uridine to cytidine when said uridine is disposed within a double stranded nucleic acid structure of at least 10 base pairs, at least four nucleotides inward from each terminus of said double stranded structure, by converting a target uridine disposed within said RNA molecule to cytidine, said method comprising:
   a) providing a single stranded complementary nucleic acid at least 10 nucleotides in length, having a sequence complementary to a segment of said RNA molecule comprising said target uridine flanked on both sides by at least four nucleotides;
   b) introducing said complementary nucleic acid into said cultured cell, allowing hybridization of said complementary nucleic acid to said RNA molecule, thereby forming a hybrid molecule having a double stranded structure of at least 10 base pairs, in which said target uridine is disposed at least four nucleotides inward from each terminus of said double stranded structure, the formation of said hybrid molecule promoting conversion of uridine to cytidine by said RNA editing component of said cell, resulting in said target uridine being converted to cytidine, thereby specifically editing said RNA molecule in said cultured cell.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: RNA (genomic)

( i i i ) HYPOTHETICAL: NO ( i v ) ANTI-SENSE: NO (v i) ORIGINAL SOURCE:
    (A) ORGANISM: Hepatitis delta virus (x i) SEQUENCE DESCRIPTION: SEQ ID NO:1:

AGAGUAUAUC CUAUGGAAAU CC     22

(2) INFORMATION FOR SEQ ID NO:2:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: RNA (genomic)

(i i i) HYPOTHETICAL: NO (i v) ANTI-SENSE: NO (v i) ORIGINAL SOURCE:
        (A) ORGANISM: Hepatitis delta virus (x i) SEQUENCE DESCRIPTION: SEQ ID NO:2:

GUGGAGCCAU GGGAUGCCCU UC     22

(2) INFORMATION FOR SEQ ID NO:3:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: RNA (genomic)

(i i i) HYPOTHETICAL: NO (i v) ANTI-SENSE: NO (v i) ORIGINAL SOURCE:
        (A) ORGANISM: Hepatitis delta virus (x i) SEQUENCE DESCRIPTION: SEQ ID NO:3:

GGAUUUCCAU GGGAUAUACU CU     22

(2) INFORMATION FOR SEQ ID NO:4:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:4:

CCATGGGATG     10

(2) INFORMATION FOR SEQ ID NO:5:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (i i) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

CCATAGGATG 10

( 2 ) INFORMATION FOR SEQ ID NO:6:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: RNA (genomic)

( i i i ) HYPOTHETICAL: YES ( i v ) ANTI-SENSE: NO ( x i ) SEQUENCE DESCRIPTION: SEQ ID NO:6:

GGGAAGAGUA UAUCUCUAUG GAAAUCCCU 29

( 2 ) INFORMATION FOR SEQ ID NO:7:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i v ) ANTI-SENSE: NO ( x i ) SEQUENCE DESCRIPTION: SEQ ID NO:7:

AGGGATTTCC ATAGTGATAT ACTCTTCCC 29